US007935271B2

(12) United States Patent
Harrison et al.

(10) Patent No.: US 7,935,271 B2
(45) Date of Patent: May 3, 2011

(54) COMPOSITIONS, SYSTEMS, AND/OR METHODS INVOLVING CHLORINE DIOXIDE

(76) Inventors: Ken Harrison, Madison, VA (US); Nick Blandford, Charlottesville, VA (US)

( * ) Notice: Subject to any disclaimer, the term of this patent is extended or adjusted under 35 U.S.C. 154(b) by 339 days.

(21) Appl. No.: 12/183,523

(22) Filed: Jul. 31, 2008

(65) Prior Publication Data

US 2009/0054375 A1    Feb. 26, 2009

Related U.S. Application Data

(60) Provisional application No. 60/965,870, filed on Aug. 23, 2007.

(51) Int. Cl.
*A61L 2/20* (2006.01)
*C01B 11/02* (2006.01)
*A61K 47/40* (2006.01)

(52) U.S. Cl. ............... 252/187.21; 423/477; 422/37; 514/778

(58) Field of Classification Search .................. None
See application file for complete search history.

(56) References Cited

U.S. PATENT DOCUMENTS

| | | | |
|---|---|---|---|
| 5,165,910 A | 11/1992 | Oikawa et al. | |
| 5,814,312 A | 9/1998 | Reich | |
| 6,238,643 B1 * | 5/2001 | Thangaraj et al. | 423/477 |
| 6,358,935 B1 * | 3/2002 | Beck et al. | 514/58 |
| 6,582,682 B2 * | 6/2003 | Stier | 424/53 |
| 6,689,378 B1 | 2/2004 | Sun | |
| 7,416,326 B2 | 8/2008 | Sakata | |
| 2006/0006361 A1 | 1/2006 | Callerame | |
| 2008/0023668 A1 | 1/2008 | Callerame | |

FOREIGN PATENT DOCUMENTS

| | | |
|---|---|---|
| CN | 1166362 | 12/1997 |
| CN | 1820607 | 8/2006 |
| JP | 2003326277 | 11/2003 |
| JP | 2006204445 | * 8/2006 |
| WO | WO00/12137 | 3/2000 |
| WO | WO03/093170 | 11/2003 |

OTHER PUBLICATIONS

Machine translation of JP 2006-204445, Tani et al (2006).*
Translation of CN 1820607, Xing et al (2006).*
Hedges, A. "Industrial applications of cyclodextrins" Chem. Rev. (1998) vol. 98, pp. 2035-2044.*
Translation of Tani et al, JP 2006-204445, (Aug. 10, 2006).*
Totze, "Diaphanol- and andere Chlordioxydlosungen in der zoologiscen Mikrotechnick", Jan. 1, 1993, 2 pages, MIKROKOSMOS, vol. 27.
Wimmer, "Cyclodextrins—From Ullmann's Encyclopedia of Industrial Chemistry", Jan. 15, 2003, 9 pages, Wiley-VCH Verlag GmbH & Co. KGaA, Weinheim.
Masschelein, "Preparation of Pure Chlorine Dioxide", Jun. 1, 1967, 6 pages, I&EC Product Research and Development, vol. 6 No. 2.
Xing, Abstract of "Study on Controlled Release Chlorine Dioxide Microcapsules", 2004, 1672-1098, Anhui Ligong Daxue Xuebao Bianjibu, 24 (2), 52-55, People's Republic of China.
Coope, "Electron Spin Resonance Study of ClO2 and Cl2- Adsorbed on Zeolites", 1971, Molecular Physics, 21(6), 1043-1055.
Pietrzak, "Preferred Rotation of ClO2 adsorbed on CaX and Synthetic Zeiolites", Jun. 30, 1972, Molecular Physic, 24(4), 909-911.
Shimokoshi, "Electron Spin Resonance Study of Chlorine Dioxide Adsorbed on the Alkali-Cation-Exchanged X-Type Zeolites", 1974, Journal of Physical Chemistry, 78(17), 1770-1771.
Sugihara, "Effect of Exchanged Cations upon the Electron Spin Resonance Hyperfine Splitting of Chlorine Dioxide Adsorbed on X-Type Zeolites", 1977, Journal of Physical Chemistry, 87(7), 669-673.
Click, "Techniques of Histo- and Cytochemistry", 1949, 470 pages, Interscience Publishers, Inc.; available online at http://www.archive.org/stream/techniquesofhisto031071mbp/techniquesofhist031071mbp_djvu.txt.
Grandcircuitinc.com, "Overview of Chlorine Dioxide (ClO2)", Aug. 31, 2001, 17 pages, http://www.grandcircuitinc.com/Howard%20Alliger%20-%20An%20Overall%20View%20Cl02.pdf.
Gray, "The Microtomist's Formulary and Guide", 1954, 1096 pages, The Blakiston Company, Inc.; available online at http://www.archive.org/stream/microtomistsform00gray/microtomistsform00gray_djvu.txt.
Kroshcwitz, editor, "Kirk-Othmer Encyclopedia of Chemical Technology, 4th Ed. vol. 5", 1993, p. 972, John Wiley & Sons, Inc., New York, NY.
Richards, "Studies on Arthropod Cuticle. II. Electron Microscope Studies of Extracted Cuticle", Jun. 1, 1948, pp. 212-235, The Biological Bulletin/Marine Biological Laboratory.

* cited by examiner

*Primary Examiner* — Leigh C Maier
(74) *Attorney, Agent, or Firm* — Michael Haynes PLC; Michael N. Haynes (57) ABSTRACT

Certain exemplary embodiments can provide a composition of matter comprising a solid form of chlorine dioxide complexed with a cyclodextrin. When stored, a concentration of the chlorine dioxide in the composition of matter can be retained, with respect to an initial concentration of chlorine dioxide in said composition of matter, at, for example, greater than 12% for at least 14 days. Certain exemplary embodiments can provide a method comprising releasing chlorine dioxide from a solid composition comprising chlorine dioxide complexed with a cyclodextrin.

29 Claims, 5 Drawing Sheets

| Example number | 2 | 3 | 4 | 5 | 6 | 7 | 8 | 9 | 10 |
|---|---|---|---|---|---|---|---|---|---|
| Sample identification | 10006-084A | 10006-084B | 10006-163A | 10006-167A | 10006-142 | 10006-153A | 10005-092 | 10005-099 | 10005-106 |
| alpha-Cyclodextrin concentration after mixing | 5.50% | 5.50% | 4.82% | 5.50% | 5.96% | 5.96% | 6% | 5.48% | 5.50% |
| $ClO_2$ concentration after mixing | 3900ppm | 3900ppm | 3425ppm | 3900ppm | 4531ppm | 4531ppm | 4636ppm | 4233ppm | 4645ppm |
| Complex formation time | 12 days | 12 days | 3 days | 6 days | 2 days | 3 days | 3 days | 3 days | 4 days |
| Time in Desiccator | 3 days | 3 days | 1 day | 1 day | 5 days | 4 days | 3days | 1 day | 1 day |
| $ClO_2$ concentration in complex | 4.31% | 2.78% | 5.60% | 5.30% | 3.25% | 5.05% | 4.35% | 6.60%* | 5.80% |
| % Yield from RT isolation | Not determined | Not determined | 6.70% | 25.60% | 31% | 33% | 35.90% | 29.70% | 32.10% |
| Total % yield including isolate from chilled filtrate | --- | --- | --- | --- | --- | --- | 45% | 38.30% | --- |

\* Note: this value is greater than the theoretical maximum (6.5%) for a 1:1 complex, which is likely due to experimental error, measurement error, etc.

```
┌─────────────────────────────────┐
│ Combine ClO2 and cyclodextrin   │  5100
└─────────────────────────────────┘
              ↓
┌─────────────────────────────────┐
│      Separate precipitate       │  5200
└─────────────────────────────────┘
              ↓
┌─────────────────────────────────┐
│          Bond solid             │  5300
└─────────────────────────────────┘
              ↓
┌─────────────────────────────────┐
│          Store solid            │  5400
└─────────────────────────────────┘
              ↓
┌─────────────────────────────────┐
│     Retain ClO2 concentration   │  5500
└─────────────────────────────────┘
              ↓
┌─────────────────────────────────┐
│         Release ClO2            │  5600
└─────────────────────────────────┘
              ↓
┌─────────────────────────────────┐
│      Apply ClO2 to target       │  5700
└─────────────────────────────────┘
```

FIG. 5

COMPOSITIONS, SYSTEMS, AND/OR METHODS INVOLVING CHLORINE DIOXIDE

CROSS-REFERENCE TO RELATED APPLICATIONS

This application claims priority to, and incorporates by reference herein in its entirety, pending U.S. Provisional Patent Application 60/965,870, filed 23 Aug. 2007.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Chlorine dioxide ("ClO2") can be an excellent disinfectant, and/or can be effective against a wide range of organisms. For example, ClO2 can provide excellent control of viruses and bacteria, as well as the protozoan parasites *Giardia*, *Cryptosporidium*, and/or amoeba *Naegleria gruberi* and their cysts.

In addition to disinfection, ClO2 can have other beneficial uses in water treatment, such as color, taste and odor control, and removal of iron and manganese. There are also important uses outside of water treatment, such as bleaching pulp and paper (its largest commercial use), disinfection of surfaces, and sanitization/preservation of fruits and vegetables.

ClO2 can present certain challenges, which can stem largely from its inherent physical and chemical instability. ClO2 in pure form is a gaseous compound under normal conditions. As a gas, it can be sensitive to chemical decomposition, exploding at higher concentrations and when compressed. Because ClO2 can be highly soluble in water, ClO2 can be used as a solution of ClO2 gas dissolved in water.

However, the gaseous nature of ClO2 means that it can be volatile, thus ClO2 tends to evaporate rapidly from solutions when open to the atmosphere (physical instability). This tendency can limit the practically useful concentrations of ClO2 solutions. With concentrated solutions, this rapid evaporation can generate gaseous ClO2 concentrations that can present an unpleasantly strong odor, and can pose an inhalation hazard to users. A closed container of the solution can quickly attain a concentration in the headspace of the container that is in equilibrium with the concentration in the solution. A high concentration solution can have an equilibrium headspace concentration that exceeds the explosive limits in air (considered to be about 10% by weight in air).

For these and other reasons, virtually all commercial applications to date have required that ClO2 be generated at the point of use to deal with these challenges. However, on-site generation also can have significant draw-backs, particularly in the operational aspects of the equipment and the need to handle and store hazardous precursor chemicals. It can be desirable to have additional forms of ready-made ClO2.

Certain exemplary embodiments can provide a composition of matter comprising a solid form of chlorine dioxide complexed with a cyclodextrin. When stored, a concentration of the chlorine dioxide in the composition of matter can be retained at, for example, greater than 12% for at least 14 days and/or greater than 90% for at least 80 days, with respect to an initial concentration of chlorine dioxide in said composition of matter. Certain exemplary embodiments can provide a method comprising releasing chlorine dioxide from a solid composition comprising chlorine dioxide complexed with a cyclodextrin.

Certain exemplary embodiments can provide a solid complex formed by combining ClO2 with a complexing agent such as a cyclodextrin, methods of forming the complex, and/or methods of using the complex as a means of delivering ClO2, such as essentially instantly delivering ClO2.

ClO2 is widely considered to be inherently unstable. Also, ClO2 is widely considered to be reactive with a fairly wide range of organic compounds, including glucose, the basic building block of cyclodextrins such as alpha-cyclodextrin. It is reasonable to assume that ClO2 will react with cyclodextrins in solution. Additionally, relatively impure ClO2 systems containing chlorite and/or chlorate impurities might be expected to destroy cyclodextrins due to the reactivity of chlorite/chlorate with organic compounds.

Chlorine dioxide can be generated by the method described in the OxyChem Technical Data Sheet "Laboratory Preparations of Chlorine Dioxide Solutions—Method II: Preparation of Reagent-Grade Chlorine Dioxide Solution", using nitrogen as the stripping gas.

Figure 1:
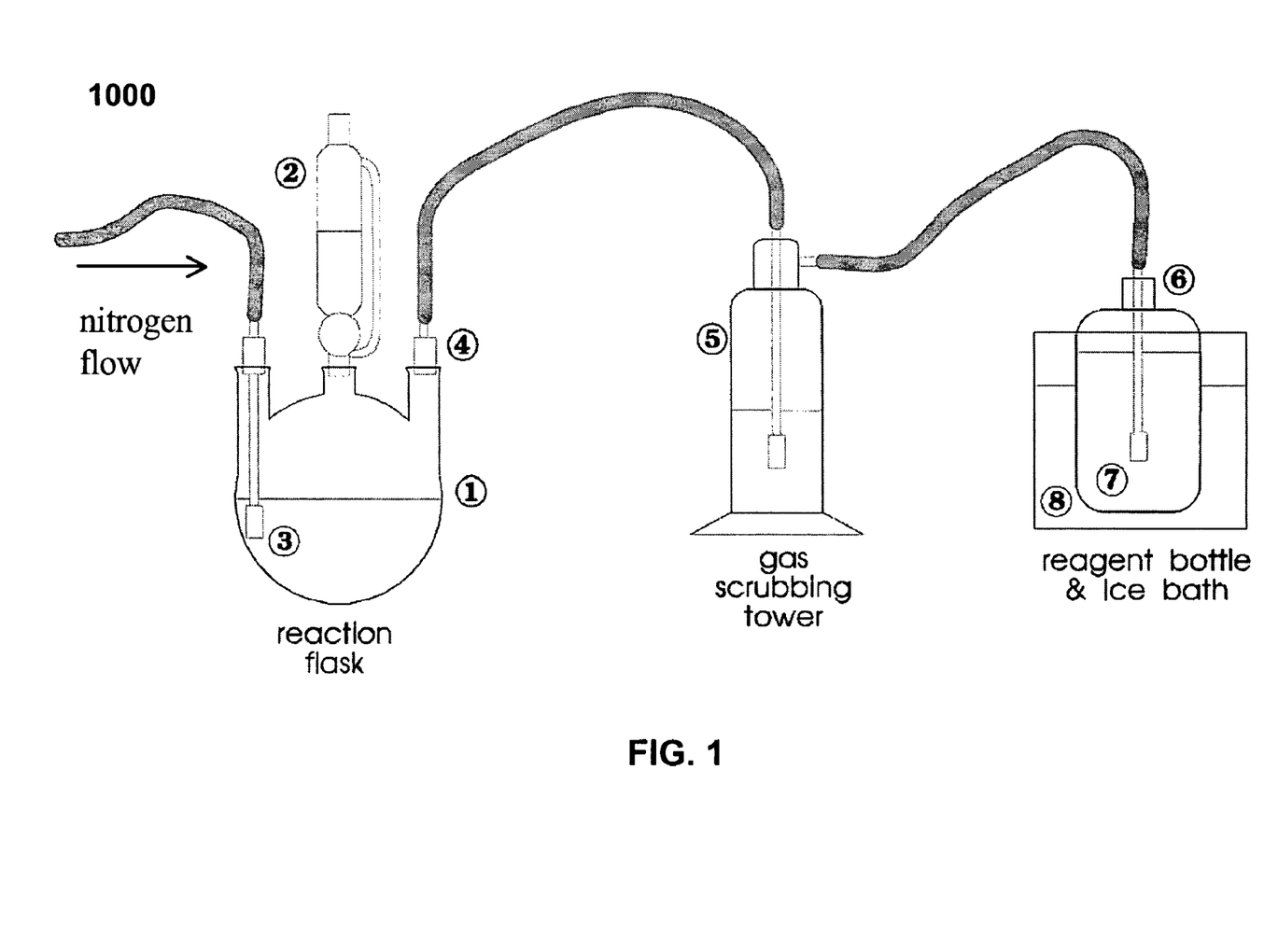
FIG. 1 is a block diagram of an exemplary embodiment of a method 1000.

That method specifies the following equipment and reagents:

three-neck reaction flask, 1-liter (1)
pressure equalizing addition funnel, 125-mls (2)
gas inlet tube, with adapter (3)
gas exit adapter (4)
gas scrubbing tower, 1-liter (5)
amber reagent bottle, 1 liter (6)
gas inlet tube, without adapter (7)
ice bath (8)
flexible tubing (rubber or Tygon®)
Technical Sodium Chlorite Solution 31.25
concentrated sulfuric acid, 36N That method specifies, inter alia, the following procedure:

Assemble the generator setup as shown in FIG. 1. To ensure airtight assembly use standard taper glassware and silicon grease if possible. Rubber stoppers are an acceptable alternative.

Fill the reaction flask and gas scrubbing tower with 500 mls of approximately 2.5% (wt) NaClO2 solution. Make certain all gas inlets are submerged. (2.5% NaClO2 solution may be prepared by diluting OxyChem Technical Sodium Chlorite Solution 31.25 1:10 with DI water).

Prepare 50 mls of 10% (vol) sulfuric acid solution and place this solution in the addition funnel. WARNING: Always add acid to water; never add water to acid.

Fill the amber reagent bottle with 500 to 750 mls. of DI water and place in an ice bath.

Turn on the air flow to the generation setup (there should be bubbles in all three solutions.) If there are not, check the setup for leaks.

Once there are no leaks, slowly add the acid solution (5 to 10 mls at a time). Wait 5 minutes between additions. Continue the air flow for 30 minutes after the final addition.

Store the chlorine dioxide solution in a closed amber bottle in a refrigerator. Properly stored solutions may be used for weeks, but should be standardized daily, prior to use, by an approved method, such as Method 4500-ClO2, Standard Methods for the Examination of Water and Wastewater., 20th Ed., APHA, Washington, D.C., 1998, pp 4-73 to 4-79.

We have unexpectedly discovered that, by bubbling sufficiently pure gaseous ClO2 diluted in nitrogen (as generated by this method) at a rate of, for example, approximately 100 ml/minute to approximately 300 ml/minute, through a near-saturated solution of alpha-cyclodextrin (approximately 11% to approximately 12% w/w) in place of plain water, at or below room temperature, a solid precipitate formed. The minimum ClO2 concentration required to obtain the solid precipitate lies somewhere in the range of approximately 500 ppm to approximately 1500 ppm. A 1:1 molar ratio of ClO2 to cyclodextrin—approximately 7600 ppm ClO2 for approximately 11% alpha-cyclodextrin—is presumed to be needed in order to complex all the alpha-cyclodextrin. We believe that the use of even more ClO2 will maximize the amount of precipitate that forms. Precipitation may begin before ClO2 addition is complete, or may take up to approximately 2 to approximately 3 days, depending on the amount of ClO2 added and the temperature of the system.

Another method of preparing this solid material is as follows. A solution of alpha-cyclodextrin is prepared. That solution can be essentially saturated (approximately 11%). A separate solution of ClO2 can be prepared by the method referenced above, potentially such that it is somewhat more concentrated than the alpha-cyclodextrin solution, on a molar basis. Then the two solutions can be combined on approximately a 1:1 volume basis and mixed briefly to form a combined solution. Concentrations and volumes of the two components can be varied, as long as the resultant concentrations in the final mixture and/or combined solution are sufficient to produce the precipitate of the complex. The mixture and/or combined solution then can be allowed to stand, potentially at or below room temperature, until the precipitate forms. The solid can be collected by an appropriate means, such as by filtration or decanting. The filtrate/supernatant can be chilled to facilitate formation of additional precipitate. A typical yield by this unoptimized process, after drying, can be approximately 30 to approximately 40% based on the starting amount of cyclodextrin. The filtrate/supernatant can be recycled to use the cyclodextrin to fullest advantage.

The collected precipitate then can be dried, such as in a desiccator at ambient pressure, perhaps using Drierite desiccant. It has been found that the optimum drying time under these conditions is approximately 24 hours. Shorter drying times under these conditions can leave the complex with unwanted free water. Longer drying times under these conditions can result in solid containing a lower ClO2 content.

Since we have observed that the residence time of the complex in a desiccating chamber has a distinct effect on the resulting ClO2 content of the dried complex, it is expected that the use of alternate methods of isolating and/or drying the complex can be employed to alter yield rates and obtain a ClO2 cyclodextrin complex with specific properties (stability, ClO2 concentration, dissolution properties, etc.) suitable for a particular application. Lyophilization and spray-drying are examples of these kinds of alternate methods, which can dry the precipitated complex, and/or isolate the complex as a dry solid from solution-phase complex, and/or from the combined precipitate/solution mixture.

Based on methods used to form other complexes with cyclodextrins, it is believed that any of several additional methods could be utilized to form the ClO2 cyclodextrin complex. Slurry complexation, paste complexation, solid phase capture, and co-solvent systems are examples of additional preparatory options. In one unoptimized example of a modified slurry process, 11 g of solid alpha-cyclodextrin was added directly to a 100 g solution of 7800 ppm ClO2 and mixed overnight. While a majority of the cyclodextrin went into solution, approximately 20% of the powder did not. This was subsequently found to have formed a complex with ClO2 that upon isolation, contained approximately 0.8% ClO2 by weight. In one unoptimized example of a solid phase capture process, ClO2 gas was generated by the method described in the OxyChem Technical Data Sheet. The ClO2 from the reaction was first passed through a chromatography column packed with a sufficient amount of Drierite to dry the gas stream. Following this drying step, 2.0 g of solid alpha-cyclodextrin was placed in-line and exposed to the dried ClO2 in the vapor phase for approximately 5 hours. The alpha-cyclodextrin was then removed, and found to have formed a complex with ClO2 containing approximately 0.75% ClO2 by weight.

This precipitate is assumed to be a ClO2/alpha-cyclodextrin complex. Cyclodextrins are known to form complexes or "inclusion compounds" with certain other molecules, although for reasons presented above it is surprising that a stable complex would form with ClO2. Such a complex is potentially characterized by an association between the cyclodextrin molecule (the "host") and the "guest" molecule which does not involve covalent bonding. These complexes are often formed in a 1:1 molecular ratio between host and guest, but other ratios are possible.

There are a number of reaction conditions that affect the process leading to the formation of the complex. Any of these conditions can be optimized to enhance the yield and/or purity of the complex. Several of these conditions are discussed below.

The pH at which the complexation takes place between ClO2 and cyclodextrin has been observed to affect the yield and ClO2 content of the resulting ClO2 complex. Therefore, this parameter might affect the stability and/or properties of the resulting complex. An approximately 11% alpha-cyclodextrin solution was combined with an approximately 9000 ppm ClO2 solution on a 1:1 molar basis and the pH immediately adjusted from approximately 3.5 to approximately 6.7 with approximately 10% NaOH. A control was set up in the same fashion with no pH adjustment after combining the approximately 11% cyclodextrin and approximately 9000 ppm ClO2 solution. The resulting yield of the pH adjusted preparation was approximately 60% lower than the control and had approximately 20% less ClO2 content by weight.

The temperature at which the complexation takes place between ClO2 and cyclodextrin has been observed to affect the yield and ClO2 content of the resulting ClO2 complex. Therefore, this parameter might affect the stability and/or properties of the resulting complex. An approximately 11% alpha-cyclodextrin solution was combined with an approximately 7800 ppm ClO2 solution on a 1:1 molar basis in 2 separate bottles. One of these was placed in a refrigerator at approximately 34° F. and the other was left at room temperature. Upon isolation and dry down of the resulting complexes, the refrigerated preparation produced approximately 25% more complex by weight and a lower ClO2 concentration.

The stirring rate and/or level of agitation during the formation of a ClO2 cyclodextrin complex has been observed to affect the yield and ClO2 content of the resulting ClO2 complex. Therefore, this parameter might affect the stability and/or properties of the resulting complex. An approximately 11% alpha-cyclodextrin solution was combined with an approximately 7800 ppm ClO2 solution on a 1:1 molar basis in 2 separate bottles. One of the bottles was placed on a magnetic stir plate at approximately 60 rpm, while the other remained undisturbed. After approximately 5 days, the precipitated complex from each was isolated and dried down. The preparation that was stirred resulted in an approximately 20% lower yield and approximately 10% lower ClO2 concentration by weight.

The addition of other compounds to the complexation mixture has been observed to affect the yield and/or ClO2 content of the resulting ClO2 complex. Therefore, the use of additives in the preparation process might affect the stability and/or properties of the resulting complex and/or lead to a ClO2 complex with properties tailored to a specific application. For example, we have found that very low concentrations of water soluble polymers (approximately 0.1% w/v), such as polyvinylpyrrolidone and carboxymethylcellulose, have resulted in ClO2 concentrations higher and lower, respectively, than that observed in a control preparation containing only cyclodextrin and ClO2. In both cases however, the yield was approximately 10% lower than the control. In another example, we found that the addition of approximately 0.5% acetic acid to the complexation mixture resulted in approximately 10% higher yield and approximately 40% lower ClO2 content.

When isolated and dried, the resulting solid typically has a granular texture, appears somewhat crystalline, with a bright yellow color, and little or no odor. It can be re-dissolved in water easily, and the resulting solution is yellow, has an odor of ClO2, and assays for ClO2. The ClO2 concentration measured in this solution reaches its maximum as soon as all solid is dissolved, or even slightly before. The typical assay method uses one of the internal methods of the Hach DR 2800 spectrophotometer designed for direct reading of ClO2. The solution also causes the expected response in ClO2 test strips such as those from Selective Micro Technologies or LaMotte Company. If a solution prepared by dissolving this complex in water is thoroughly sparged with N2 (also known as Nitrogen or $N_2$), the solution becomes colorless and contains virtually no ClO2 detectable by the assay method. The sparged ClO2 can be collected by bubbling the gas stream into another container of water.

One sample of the dried solid complex was allowed to stand in an uncovered container for approximately 30 hours before being dissolved in water, and appeared to have lost none of its ClO2 relative to a sample that was dissolved in water immediately after drying. Four portions from one batch of solid complex left in open air for periods of time ranging from approximately 0 to approximately 30 hours before being re-dissolved in water all appeared to have about the same molar ratio of ClO2 to alpha-cyclodextrin. Other batches appeared to have somewhat different ratios of ClO2 to alpha-cyclodextrin. This difference may simply reflect differences in sample dryness, but it is known that cyclodextrin-to-guest ratios in other cyclodextrin complexes might vary with differences in the process by which the complex was formed. However, samples of the present complex prepared by an exemplary embodiment tended to contain close to, but to date not greater than, a 1:1 molar ratio of ClO2 to cyclodextrin. That is, their ClO2 content approached the theoretical limit for a 1:1 complex of approximately 6.5% by weight, or approximately 65,000 ppm, ClO2. Assuming that a 1:1 molar ratio represents the ideal form of the pure complex, the ratio of ClO2 to cyclodextrin can be targeted as close to 1:1 as possible, to serve as an efficient ClO2 delivery vehicle. However, solid complexes with a net ClO2 to cyclodextrin ratio of less than 1:1 can be desirable in some cases. (We believe such a material is probably a mixture of 1:1 complex plus uncomplexed cyclodextrin, not a complex with a molar ratio of less than 1:1.)

An aqueous solution of ClO2 having such a high concentration (e.g., approaching approximately 65,000 ppm) can pose technical and/or safety challenges in handling, such as rapid loss of ClO2 from the solution into the gas phase (concentrated and therefore a human exposure risk), and/or potentially explosive vapor concentrations in the headspace of a container in which the solution is contained. The solid appears not to have these issues. Release into the gas phase is relatively slow, posing little exposure risk from the complex in open air. The lack of significant odor can be an important factor in the users' sense of safety and/or comfort in using the solid. For example, a small sample has been left in the open air for approximately 72 hours, with only an approximately 10% loss of ClO2. At such a slow rate, users are unlikely to experience irritation or be caused to feel concern about exposure. Gas-phase ClO2 concentration in the headspace of a closed container of the complex can build up over time, but appears not to attain explosive concentrations. Even solid complex dampened with a small amount of water, so that a "saturated" solution is formed, to date has not been observed to create a headspace ClO2 concentration in excess of approximately 1.5% at room temperature. It is commonly believed that at least a 10% concentration of ClO2 in air is required for explosive conditions to exist.

The freshly-prepared complex is of high purity, since it is obtained by combining only highly pure ClO2 prepared by OxyChem Method II, cyclodextrin, and water. Some cyclodextrins are available in food grade, so the complex made with any of these is suitable for treatment of drinking water and other ingestible materials, as well as for other applications. Other purity grades (technical, reagent, pharmaceutical, etc.) of cyclodextrins are available, and these could give rise to complexes with ClO2 that would be suitable for still other applications.

In certain embodiments, the solid complex can be quickly and conveniently dissolved directly in water that is desired to be treated. Alternatively, the solid can be dissolved, heated, crushed, and/or otherwise handled, processed, and/or treated to form, and/or release from the solid, a solution, such as an aqueous chlorine dioxide solution, and/or another form of ClO2, such as a ClO2 vapor, that then can be used for disinfecting surfaces, solids, waters, fluids, and/or other materials. For example, solutions of ClO2 prepared by dissolving the complex in water, either the water to be treated or an intermediate solution, can be used for any purpose known in the art for which a simple aqueous solution of comparable ClO2 concentration would be used, insofar as this purpose is compatible with the presence of the cyclodextrin. These uses can include disinfection and/or deodorization and/or decolorization of: drinking water, waste water, recreational water (swimming pools, etc.), industrial reuse water, agricultural irrigation water, as well as surfaces, including living tissues (topical applications) and foods (produce, meats) as well as inanimate surfaces, etc.

It is anticipated that the complex can be covalently bound, via the cyclodextrin molecule, to another substrate (a polymer for example) for use in an application where multiple functionality of a particular product is desired. For example, such a complex bound to an insoluble substrate can, upon contact with water, release its ClO2 into solution while the cyclodextrin and substrate remain in the solid phase.

It has been found that this solid complex ordinarily experiences a slow release of ClO2 gas into the air. Conditions can be selected such that the concentration level of the ClO2 released into the air is low enough to be safe (a condition suggested by the lack of conspicuous odor) but at a high enough concentration to be efficacious for disinfection and/or odor control in the air, and/or disinfection of surfaces or materials in contact with the air.

The solid complex can release ClO2 directly, via the gas phase, and/or via moisture that is present, into other substances. The solid can be admixed with such substances, such as by mixing powdered and/or granular solid complex with the other substances in powdered and/or granular form. The solid complex can be applied to a surface, such as skin and/or other material, either by "rubbing in" a sufficiently fine powder of the complex, and/or by holding the solid complex against the surface mechanically, as with a patch and/or bandage. The substance receiving the ClO2 from the complex can do so as a treatment of the substance and/or the substance can act as a secondary vehicle for the ClO2.

In some instances, the complex can impart different and/or useful reactivity/properties to ClO2. By changing its electronic and/or solvation environment, the reactivity of complexed ClO2 will almost certainly be quantitatively, and perhaps qualitatively, different.

Figure 2:
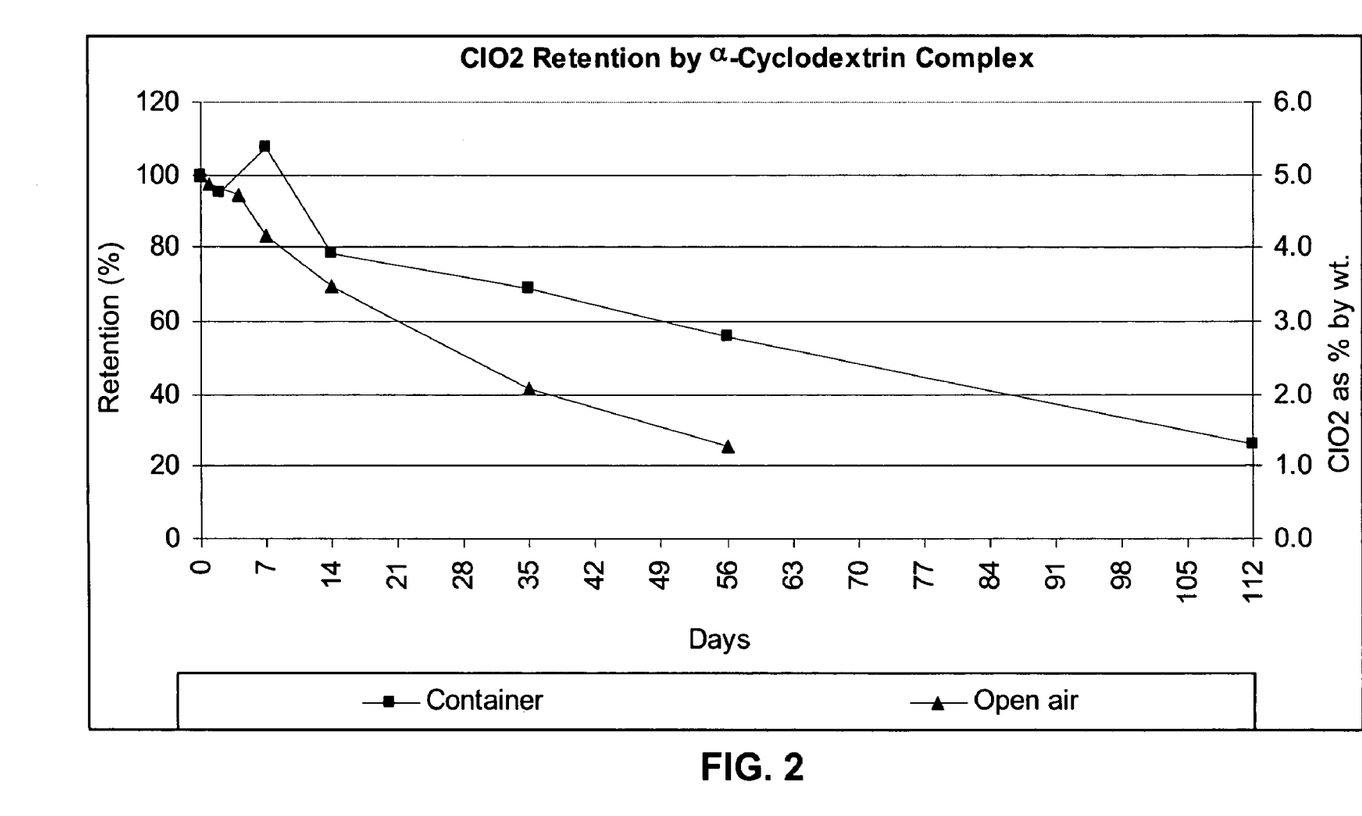
FIG. 2 is a graph of an exemplary embodiment's ability to retain ClO2.

FIG. 2 illustrates the ability of an exemplary complex to retain ClO2 when stored at room temperature, either in the open air (an uncapped jar) or in a closed and/or substantially ClO2-impermeable container with relatively little headspace. It appears that ClO2 is retained somewhat more effectively in the closed, low-headspace container, and it may be possible to improve ClO2 retention further by reducing the headspace further. However, ClO2 retention is remarkable in either case, considering that the complex is an essentially waterless medium containing a reactive gaseous molecule.

Figure 3:
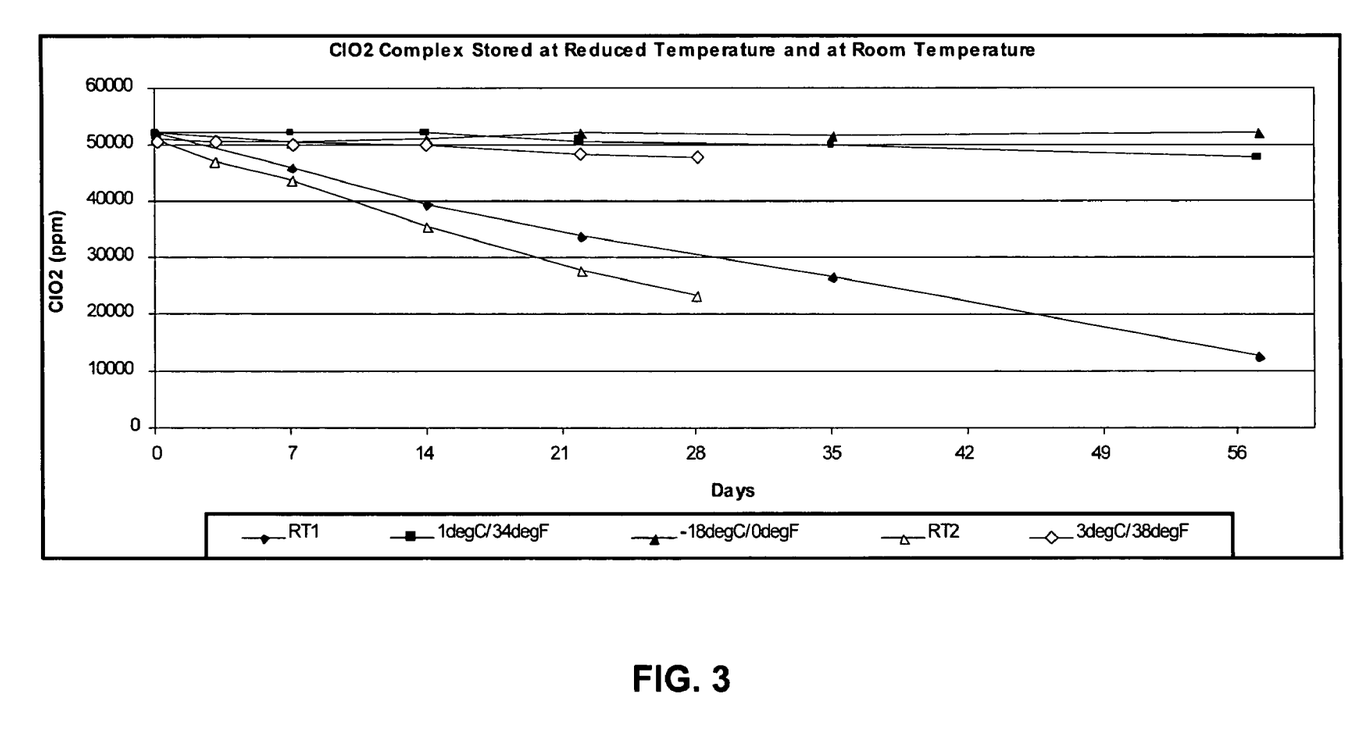
FIG. 3 is a graph of an exemplary embodiment's ability to retain ClO2.

Early indications are that ClO2 retention can be greatly enhanced by cold storage. FIG. 3 illustrates retention by samples stored at room temperature (RT) (at approximately 20 C to approximately 26 C) compared to those stored in a refrigerator (at approximately 1 C and at approximately 3 C) and those stored in a freezer (at approximately −18 C). For example, to one of ordinary skill in the art, FIG. 3 illustrates that a sample stored at room temperature for 14 days, retained greater than 0 percent to greater than 65 percent, including all values and sub-ranges therebetween (e.g., 6.157, 12, 22.7, 33, 39.94, 45, etc., percent), and in fact approximately 70 percent of its original ClO2 content. Another sample, when stored at room temperature for 56 days, retained greater than 0 percent to greater than 20 percent, including all values and sub-ranges therebetween, and in fact approximately 24 percent of its original ClO2 content. As another example, FIG. 3 illustrates that a sample stored at approximately 3 C for 28 days retained greater than 0 percent to greater than 90 percent, including all values and sub-ranges therebetween, and in fact approximately 94 percent of its original ClO2 content. FIG. 3 also illustrates that a sample stored at approximately 1 C for at least 35 days retained greater than 0 percent to greater than 95 percent, including all values and sub-ranges therebetween, and in fact approximately 96 percent of its original ClO2 content. One of ordinary skill can determine additional retention amounts, percentages, and times by a cursory review of FIG. 3. While not wishing to be bound by any particular theory, these retention results might be due in part to the fact that ClO2 in the pure state, though a gas at room temperature, is a liquid at temperatures below 11 C (down to −59 C, at which temperature it freezes into a solid).

The solid complex can be packaged and/or stored in a range of forms and packages. Forms can include granulations/powders essentially as recovered from the precipitation process. The initially obtained solid complex can be further processed by grinding and/or milling into finer powder, and/or pressing into tablets and/or pucks and/or other forms known to the art. Other materials substantially unreactive toward ClO2 can be combined with the solid complex to act as fillers, extenders, binders, and/or disintegrants, etc.

Suitable packages are those that can retain gaseous ClO2 to a degree that provides acceptable overall ClO2 retention, consistent with its inherent stability, as discussed above, and/or that provide adequate protection from moisture. Suitable materials to provide high ClO2 retention can include glass, some plastics, and/or unreactive metals such as stainless steel. The final form of the product incorporating the solid complex can include any suitable means of dispensing and/or delivery, such as, for example, enclosing the solid in a dissolvable and/or permeable pouch, and/or a powder/solid metering delivery system, and/or any other means known in the art.

Other cyclodextrins: Most of the above material relates to alpha-cyclodextrin and the complex formed between it and ClO2. This is the only ClO2/cyclodextrin complex yet isolated. We believe that beta-cyclodextrin may form a complex with ClO2, which techniques readily available to us have not been able to isolate. Whereas the complex with alpha-cyclodextrin is less soluble than alpha-cyclodextrin alone, leading to ready precipitation of the complex, it may be that the ClO2/beta-cyclodextrin complex is more soluble than beta-cyclodextrin alone, making isolation more difficult. Such solubility differences are known in the art surrounding cyclodextrin complexes. Techniques such as freeze-drying may be able to isolate the complex in the future.

However indirect evidence for the complex has been observed. Beta-cyclodextrin has a known solubility in water. If the water contains a guest substance that produces a cyclodextrin complex more soluble than the cyclodextrin alone, more of the cyclodextrin will dissolve into water containing that guest than into plain water. This enhanced solubility has been observed for beta-cyclodextrin in water containing ClO2. Two separate 100 g slurries of beta-cyclodextrin solutions were prepared. The control solution contained 5% beta-cyclodextrin (w/w) in ultrapure water, and the other contained 5% beta-cyclodextrin (w/w) in 8000 ppm ClO2. Both slurries were mixed at 200 rpm for 3 days, at which time the undissolved beta-cyclodextrin was isolated from both solutions and dried for 2 days in a desiccator. The weight of the dried beta-cyclodextrin from the ClO2 containing slurry was 0.32 g less than the control slurry indicating that a soluble complex might exist between the beta-cyclodextrin and ClO2 in solution. It is believed, by extension, that ClO2 might form complexes with gamma-cyclodextrin and/or chemically derivatized versions of the natural (alpha- ("α"), beta- ("β"), and gamma- ("γ")) cyclodextrins. In the case of beta- and/or gamma-cyclodextrin and/or other cyclodextrins having internal cavities larger than that of alpha-cyclodextrin, it might be that the complex(es) formed with ClO2 will incorporate numbers of ClO2 molecules greater than one per cyclodextrin molecule.

Related inclusion complex formers: It is expected by extension of the observed cyclodextrin complexes that some other molecules known to form inclusion compounds will also complex ClO2. In particular, cucurbiturils are molecules known primarily for having ring structures that accommodate smaller molecules into their interior cavities. These interior cavities are of roughly the same range of diameters as those of the cyclodextrins. It is anticipated that combining the appropriate cucurbituril(s) and ClO2 under correct conditions will produce cucurbituril/ClO2 complex(es), whose utility can be similar to that of cyclodextrin/ClO2 complexes.

EXAMPLES

Example 1

Complex Preparation by Generation Process

ClO2 generated by the OxyChem Method II referenced above was bubbled as a stream mixed with nitrogen, at a rate of approximately 100-300 ml per minute, into an approximately 120 mL serum bottle containing approximately 100 g of approximately 11% (by weight) alpha-cyclodextrin solution at RT. Precipitation of the complex was observed to begin within approximately 1 hour, with ClO2 ultimately reaching a concentration of approximately 7000 ppm or more in the solution. Precipitation occurred very rapidly, and over the course of approximately 10 minutes enough complex was formed to occupy a significant volume of the bottle. The bottle was capped and placed in the refrigerator to facilitate further complex formation. After approximately 1 week the solid was removed from the solution onto filter paper and dried in a desiccator with Drierite for approximately 4 days. Yield was approximately 50% (by weight of starting cyclodextrin), and ClO2 concentration in the complex was approximately 1.8%.

Examples 2-10

Complex Preparation by Combining Solutions

Figure 4:
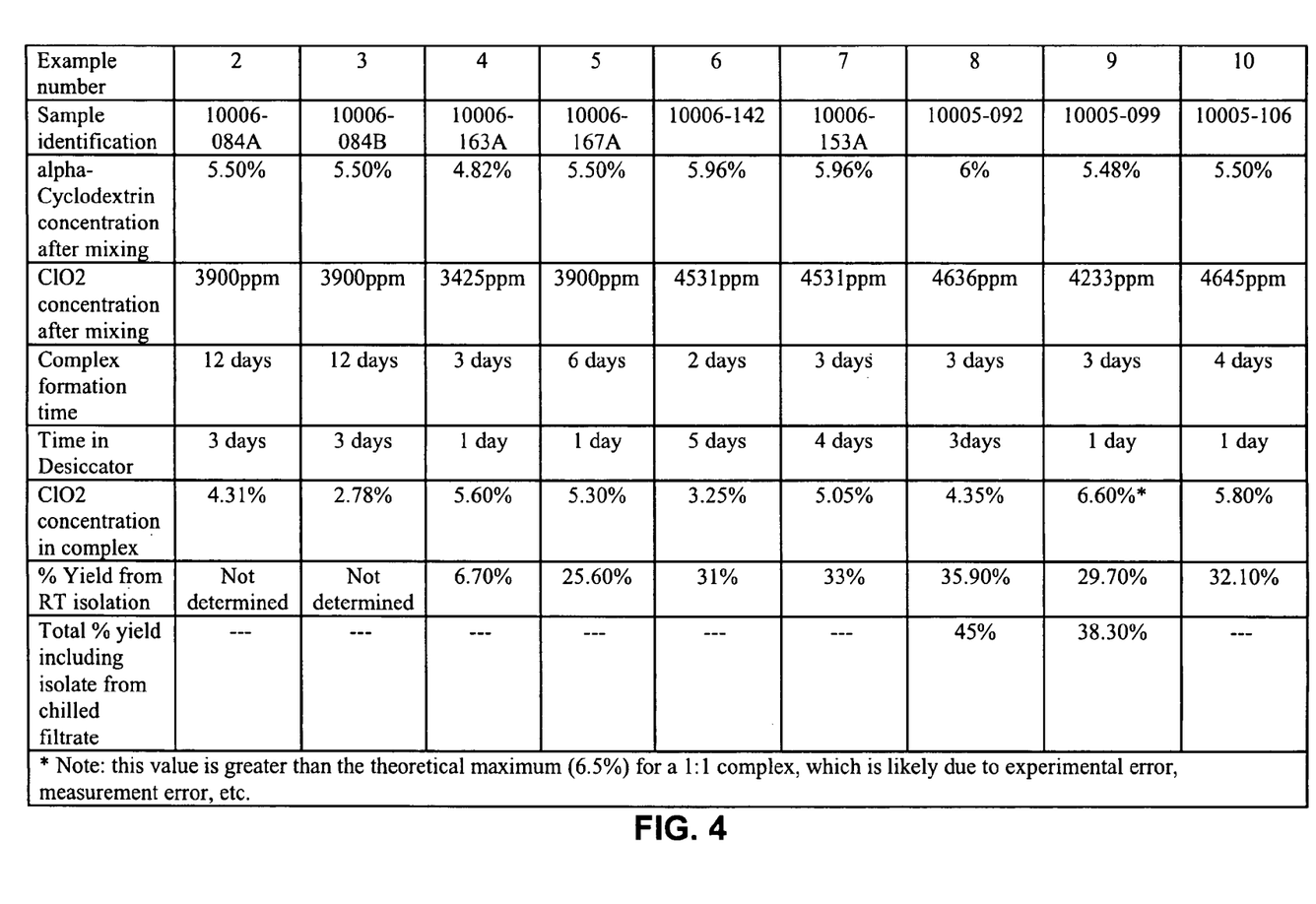
FIG. 4 is a table describing specifics of individual examples.

The general method used was as follows. See FIG. 4 for a table describing specifics of individual examples. A nearly saturated (approximately 11%) solution of alpha-cyclodextrin was prepared. A separate solution of ClO2 was prepared by OxyChem Method II, such that it was somewhat more concentrated than the alpha-cyclodextrin solution, on a molar basis. The two solutions were combined at approximately a 1:1 volume basis, i.e., approximately 500 ml of each, and mixed briefly to combine thoroughly. The mixture was then allowed to stand at room temperature, until the precipitate formed. Stirring during precipitation did not appear to improve the yield or quality of product. The solid was collected by filtration or decanting. In certain cases the filtrate/supernatant was chilled to facilitate formation of additional precipitate. The collected precipitate was then dried in a desiccator at ambient pressure using Drierite desiccant.

Additional Examples

Other experiments showed a wide variety in initial ClO2 concentrations in freshly prepared complex. For example, in several experiments, complex formed by the combining solutions approach yielded ClO2 concentrations such as 1.8% and 0.9%. In other experiments, complex formed by the generation method in which the ClO2 was captured in an ice-chilled cyclodextrin solution yielded 0.2% ClO2.

Additional experiments at room temperature resulted in a wide variety of ClO2 retention results. For example, when complex formed by the combining solutions approach was sealed in approximately 10 ml vials with a nitrogen blanket, approximately 56% of the original ClO2 concentration was retained after 35 days, and approximately 31% was retained after 56 days. As another example, when complex formed by the generation method was left open to the air in a dark storage area, approximately 42% of the original ClO2 concentration was retained after 35 days, and approximately 25% was retained after 56 days. As yet another example, when complex formed by the generation method was sealed in approximately 10 ml clear glass vials with a nitrogen blanket and stored under white fluorescent light, approximately 13% of the original ClO2 concentration was retained after 14 days. As still another example, when complex formed by the generation method was stored in an approximately 2 ounce jar covered with Parafilm, approximately 6% of the original ClO2 concentration was retained after 59 days.

Further experiments at refrigerator temperature (approximately 1 degree C.) also resulted in a wide variety of ClO2 retention results with respect to the original ClO2 concentration, including 91% after 30 days, 95% after 85 days, and 100% after 74 days.

Figure 5:
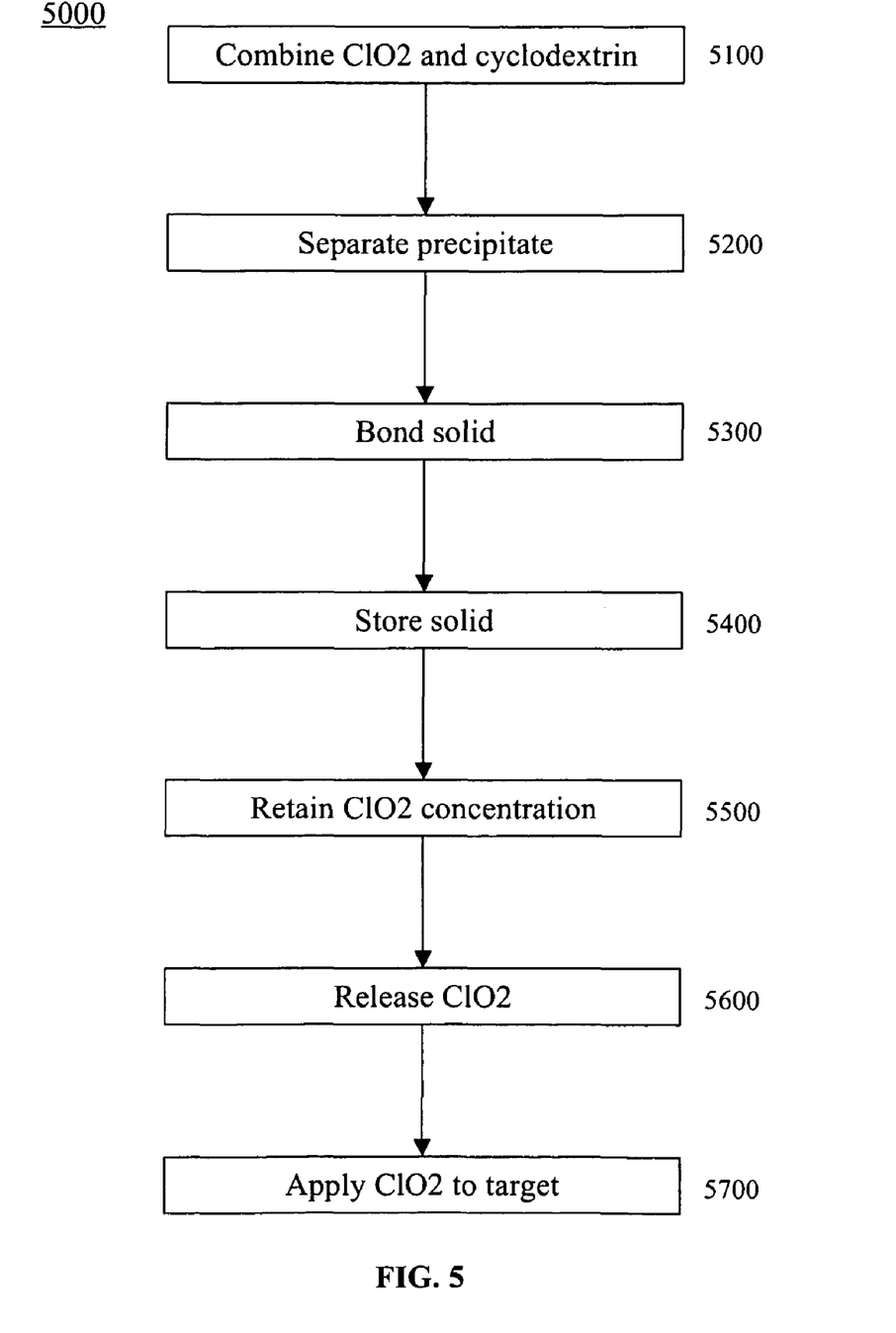
FIG. 5 is a flowchart of an exemplary embodiment of a method 5000.

FIG. 5 is a flowchart of an exemplary embodiment of a method 5000. At activity 5100, a solution of cyclodextrin can be combined with a solution of chlorine dioxide, such as on an approximately 1:1 molar basis, to form a combined solution, which can form and/or precipitate a solid and/or solid complex comprising the chlorine dioxide complexed with the cyclodextrin. At activity 5200, the precipitate can be separated from the combined solution, and/or the combined solution and/or precipitate can be dried, lyophilized, and/or spray-dried. At activity 5300, the resulting solid complex can be bonded, such as via covalent bonding, to, for example, a substrate and/or a polymer. Bonding of the complex via the cyclodextrin to a substrate might be possible at this stage, but it might be more feasible to bond the cyclodextrin to the substrate before forming the complex with ClO2. At activity 5400, the solid complex can be stored, such as in a closed and/or substantially ClO2-impermeable container, at a desired temperature, such as at ambient, room, refrigerated, and/or heated temperature. At activity 5500, the solid complex can retain a concentration of chlorine dioxide, with respect to an initial concentration of chlorine dioxide in the complex, at, for example, greater than 60% for at least 42 days. At activity 5600, the chlorine dioxide can be released from the complex, such as by dissolving the complex in water. At activity 5700, the chlorine dioxide can be applied to a target, such as a volume of liquid, such as water, a fluid, and/or a solid, such as a surface.

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
activity—an action, act, step, and/or process or portion thereof.
adapted to—made suitable or fit for a specific use or situation.
air—the earth's atmospheric gas.
and/or—either in conjunction with or in alternative to.
apparatus—an appliance or device for a particular purpose
apply—to place in contact with and/or close physical proximity to and/or to lay and/or spread on.
approximately—about and/or nearly the same as.
aqueous—related to and/or containing water
at least—not less than.

bond—to attach and/or fasten.

can—is capable of, in at least some embodiments.

chlorine dioxide—a highly reactive oxide of chlorine with the formula ClO2 or $ClO_2$, it can appear as a reddish-yellow gas that crystallizes as orange crystals at −59° C., and it is a potent and useful oxidizing agent often used in water treatment and/or bleaching.

closed—having boundaries, enclosed.

combine—to join, unite, mix, and/or blend.

complex—a compound comprising a reversible association of molecules, atoms, and/or ions.

composition of matter—a combination, reaction product, compound, mixture, formulation, material, and/or composite formed by a human and/or automation from two or more substances and/or elements.

compound—composed of two or more substances, parts, elements, and/or ingredients.

comprising—including but not limited to, what follows.

concentration—measure of how much of a given substance there is mixed, dissolved, contained, and/or otherwise present in and/or with another substance.

container—an enclosure adapted to retain a filling and having a closable opening via which a filling can be introduced. Examples of a container include a vial, syringe, bottle, flask, etc.

covalently—characterized by a combination of two or more atoms by sharing electrons so as to achieve chemical stability under the octet rule. Covalent bonds are generally stronger than other bonds.

cyclodextrin—any of a group of cyclic oligosaccharides, composed of 5 or more α-D-glucopyranoside units linked 1→4, as in amylose (a fragment of starch), typically obtained by the enzymatic hydrolysis and/or conversion of starch, designated α-, β-, and γ-cyclodextrins (sometimes called cycloamyloses), and used as complexing agents and in the study of enzyme action. The 5-membered macrocycle is not natural. Recently, the largest well-characterized cyclodextrin contains 32 1,4-anhydroglucopyranoside units, while as a poorly characterized mixture, even at least 150-membered cyclic oligosaccharides are also known. Typical cyclodextrins contain a number of glucose monomers ranging from six to eight units in a ring, creating a cone shape, typically denoted as: α-cyclodextrin: six-membered sugar ring molecule; β-cyclodextrin: seven sugar ring molecule; and γ-cyclodextrin: eight sugar ring molecule.

deliver—to provide, carry, give forth, and/or emit.

device—a machine, manufacture, and/or collection thereof.

dissolve—to make a solution of, as by mixing with a liquid and/or to pass into solution.

dry—(v) to lose and/or remove moisture from; (adj) substantially free from moisture or excess moisture; not moist; not wet.

food grade—determined by the US Food and Drug Administration as safe for use in food.

form—(v) to construct, build, generate, and/or create; (n) a phase, structure, and/or appearance.

from—used to indicate a source.

further—in addition.

greater—larger and/or more than.

initial—at a beginning.

lyophilize—to dry by freezing in a high vacuum.

may—is allowed and/or permitted to, in at least some embodiments.

method—a process, procedure, and/or collection of related activities for accomplishing something.

mix—to combine (substances, elements, things, etc.) into one mass, collection, or assemblage, generally with a thorough blending of the constituents.

molar ratio—the ratio of moles of one substance to moles of another substance.

not—a negation of something.

pharmaceutical grade—determined by the US Food and Drug Administration as safe for use in drugs.

plurality—the state of being plural and/or more than one.

polymer—any of numerous natural and synthetic compounds of usually high molecular weight consisting of up to millions of repeated linked units, each a relatively light and simple molecule.

precipitate—a substance separated in solid form and/or phase from a solution.

predetermined—established in advance.

probability—a quantitative representation of a likelihood of an occurrence.

release—to let go and/or free from something that restrains, binds, fastens, and/or holds back.

repeatedly—again and again; repetitively.

result—an outcome and/or consequence of a particular action, operation, and/or course.

retain—to restrain, keep, and/or hold.

said—when used in a system or device claim, an article indicating a subsequent claim term that has been previously introduced.

separate—to disunite, space, set, or keep apart and/or to be positioned intermediate to.

set—a related plurality.

solid—neither liquid nor gaseous, but instead of definite shape and/or form.

solution—a substantially homogeneous molecular mixture and/or combination of two or more substances.

spray dry—to eject a liquid stream into a hot vapor stream, thereby separating a solute or suspension in the liquid as a solid and the solvent and/or remaining liquid into a vapor. The solid is usually collected in a drum or cyclone.

store—to take in, hold, and/or secure.

substantially—to a great extent or degree.

substrate—an underlying layer.

surface—the outer boundary of an object or a material layer constituting or resembling such a boundary.

system—a collection of mechanisms, devices, machines, articles of manufacture, processes, data, and/or instructions, the collection designed to perform one or more specific functions.

technical grade—containing small amounts of other chemicals, hence slightly impure.

temperature—measure of the average kinetic energy of the molecules in a sample of matter, expressed in terms of units or degrees designated on a standard scale.

utilize—to use and/or put into service.

via—by way of and/or utilizing.

water—a transparent, odorless, tasteless liquid containing approximately 11.188 percent hydrogen and approximately 88.812 percent oxygen, by weight, characterized by the chemical formula $H_2O$, and, at standard pressure (approximately 14.7 psia), freezing at approximately 32° F. or 0 C and boiling at approximately 212° F. or 100 C.

weight—a force with which a body is attracted to Earth or another celestial body, equal to the product of the object's mass and the acceleration of gravity; and/or a factor assigned to a number in a computation, such as in determining an average, to make the number's effect on the computation reflect its importance.

when—at a time.

wherein—in regard to which; and; and/or in addition to.

with respect to—in relation to.

Notes

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive.

What is claimed is:

1. A composition of matter comprising:
a solid form of chlorine dioxide complexed with alpha-cyclodextrin.

2. The composition of matter of claim 1, wherein:
said alpha-cyclodextrin is not covalently bonded to the chlorine dioxide.

3. The composition of matter of claim 1, wherein:
a molar ratio of said alpha-cyclodextrin to said chlorine dioxide in said composition of matter is approximately 1:1.

4. The composition of matter of claim 1, wherein:
a concentration of chlorine dioxide in said composition of matter is greater than 4.9 percent by weight.

5. The composition of matter of claim 1, wherein:
a concentration of chlorine dioxide in said composition of matter is at least 0.2 percent by weight.

6. The composition of matter of claim 1, wherein:
when stored, a concentration of chlorine dioxide in said composition of matter is retained, with respect to an initial concentration of chlorine dioxide in said composition of matter, at greater than 12% for at least 14 days.

7. The composition of matter of claim 1, wherein:
when stored, a concentration of chlorine dioxide in said composition of matter is retained, with respect to an initial concentration of chlorine dioxide in said composition of matter, at greater than 31% for at least 56 days.

8. The composition of matter of claim 1, wherein:
when stored, a concentration of chlorine dioxide in said composition of matter is retained, with respect to an initial concentration of chlorine dioxide in said composition of matter, at greater than 90% for at least 80 days.

9. The composition of matter of claim 1, wherein:
when stored in a closed container at a temperature of approximately 1° C. or lower, a concentration of chlorine dioxide in said composition of matter is retained, with respect to an initial concentration of chlorine dioxide in said composition of matter, at greater than 90% for at least 35 days.

10. The composition of matter of claim 1, wherein:
when stored in a closed container at a temperature of approximately 3 C or lower, a concentration of chlorine dioxide in said composition of matter is retained, with respect to an initial concentration of chlorine dioxide in said composition of matter, at greater than 50% for at least 28 days.

11. The composition of matter of claim 1, wherein:
said alpha-cyclodextrin is food grade.

12. The composition of matter of claim 1, wherein:
said alpha-cyclodextrin is pharmaceutical grade.

13. The composition of matter of claim 1, wherein:
said alpha-cyclodextrin is technical grade.

14. A method comprising:
combining a solution of alpha-cyclodextrin with a solution of chlorine dioxide on an approximately 1:1 molar ratio to form a combined solution; and
separating a resulting precipitate, said precipitate comprising a solid form of said chlorine dioxide complexed with said alpha-cyclodextrin.

15. The method of claim 14, further comprising:
drying said combined solution.

16. The method of claim 14, further comprising:
drying said precipitate.

17. The method of claim 14, further comprising:
lyophilizing said combined solution and/or said precipitate.

18. The method of claim 14, further comprising:
spray-drying said combined solution.

19. A method comprising:
forming a solid complex comprising chlorine dioxide and alpha-cyclodextrin.

20. The method of claim 19, further comprising:
covalently bonding said solid complex to a substrate.

21. The method of claim 19, further comprising:
covalently bonding said alpha-cyclodextrin to a substrate before said forming a solid complex.

22. The method of claim 19, further comprising:
covalently bonding said solid complex to a polymer.

23. A method comprising:
storing, in a closed container, a composition of matter comprising a solid form of chlorine dioxide complexed with alpha-cyclodextrin, a concentration of chlorine dioxide in said composition of matter retained, with respect to an initial concentration of chlorine dioxide in said composition of matter, at greater than 31% for at least 56 days.

24. A method comprising:
dissolving in water a composition of matter comprising a solid form of chlorine dioxide complexed with alpha-cyclodextrin.

25. A method comprising:
forming an aqueous chlorine dioxide solution by mixing in water a solid form of chlorine dioxide complexed with alpha-cyclodextrin.

26. The method of claim 25, further comprising:
applying said aqueous chlorine dioxide solution to water.

27. The method of claim 25, further comprising:
applying said aqueous chlorine dioxide solution to a surface.

28. The method of claim 25, further comprising:
applying said aqueous chlorine dioxide solution to air.

29. A method comprising:
releasing chlorine dioxide from a solid composition comprising chlorine dioxide complexed with alpha-cyclodextrin.

* * * * *